US010161934B2

(12) United States Patent
Laury-Kleintop et al.

(10) Patent No.: US 10,161,934 B2
(45) Date of Patent: Dec. 25, 2018

(54) BIOCOATED PIEZOELECTRIC BIOSENSOR PLATFORM FOR POINT-OF-CARE DIAGNOSTIC USE

(75) Inventors: Lisa Laury-Kleintop, Ambler, PA (US); Herman Rutner, Hatboro, PA (US)

(73) Assignee: Aviana Molecular Technologies, LLC, Orlando, FL (US)

( * ) Notice: Subject to any disclaimer, the term of this patent is extended or adjusted under 35 U.S.C. 154(b) by 1175 days.

(21) Appl. No.: 14/241,333

(22) PCT Filed: Aug. 27, 2012

(86) PCT No.: PCT/US2012/052583
§ 371 (c)(1),
(2), (4) Date: Aug. 26, 2014

(87) PCT Pub. No.: WO2013/033049
PCT Pub. Date: Mar. 7, 2013

(65) Prior Publication Data
US 2015/0111765 A1    Apr. 23, 2015

Related U.S. Application Data

(60) Provisional application No. 61/527,716, filed on Aug. 26, 2011.

(51) Int. Cl.
*G01N 33/551* (2006.01)
*G01N 33/543* (2006.01)
(Continued)

(52) U.S. Cl.
CPC ....... *G01N 33/54306* (2013.01); *B05D 3/142* (2013.01); *G01D 5/14* (2013.01);
(Continued)

(58) Field of Classification Search
None
See application file for complete search history.

(56) References Cited

U.S. PATENT DOCUMENTS 3,949,323 A    4/1976  Bierlein et al.
4,236,893 A   12/1980  Rice
(Continued)

FOREIGN PATENT DOCUMENTS

EP    0223221      5/1987
EP    0416730 A2 * 3/1991  ....... G01N 33/54353
(Continued)

OTHER PUBLICATIONS

Vikholm, Inger, "Self-Assembly of Antibody fragments and Polymers onto Gold for Immunosensing," Sensors and Actuators B, vol. 106, dated Sep. 30, 2004, pp. 311-316.
(Continued)

*Primary Examiner* — Christopher L Chin
(74) *Attorney, Agent, or Firm* — Burns & Levinson, LLP; Richard B. Emmons

(57) ABSTRACT

Biosensor components (chips) are described based on direct biocoating processes that result in the tenacious and stable, noncovalent (believed to be chemisorptive) binding of anchor substances such as avidin(s) other proteins having specific binding partners or oligo- or poly-nucleotides onto any piezo-electrically active crystal surface. The resulting platform technology can be developed for a variety of biosensors with specific applications in biological assays. The table mono layers of the anchor substances forms reactive layers, ready to bind a capture reagent such as a biot-inylated antibody for capture and detection of analytes in biologic fluid samples. Although the processes described herein can be performed on any type of piezoelectric material in any number of configurations, some embodiments are directed to a biosensor with the foregoing biocoating onto a
(Continued)

Figure 1:
Figure 1:
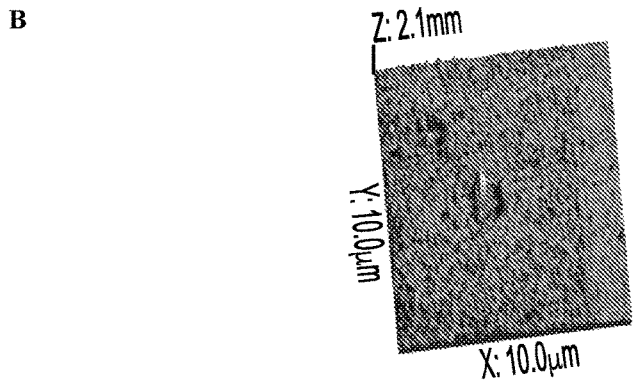
Figure 1:
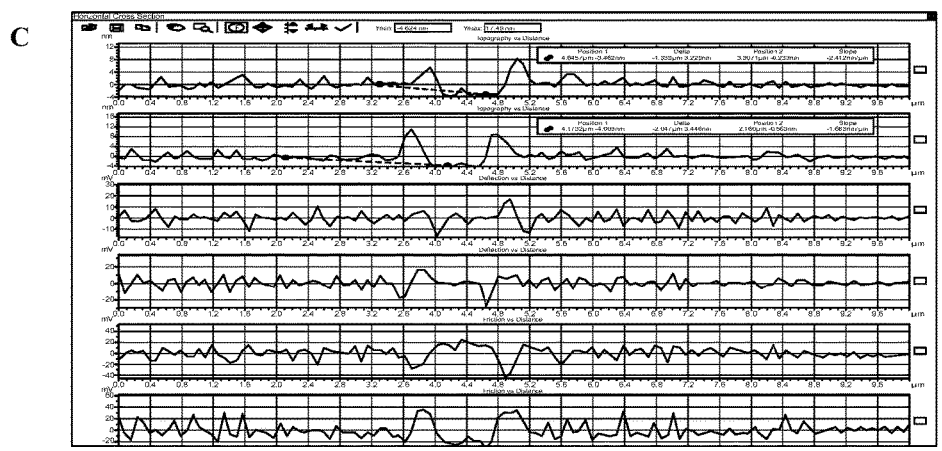

particular acoustic plate mode biosensor and where the interdigitated transducers (IDTs) are present on the opposite side of the crystal's biocoated film.

18 Claims, 11 Drawing Sheets

(51) Int. Cl.
| | |
|---|---|
| G01N 29/02 | (2006.01) |
| H01L 41/113 | (2006.01) |
| H01L 41/253 | (2013.01) |
| B05D 3/14 | (2006.01) |
| G01D 5/14 | (2006.01) |
| G01N 29/22 | (2006.01) |
| G01N 29/34 | (2006.01) |
| G01N 29/36 | (2006.01) |
| G01N 33/569 | (2006.01) |

(52) U.S. Cl.
 CPC ........... *G01N 29/02* (2013.01); *G01N 29/022* (2013.01); *G01N 29/22* (2013.01); *G01N 29/34* (2013.01); *G01N 29/36* (2013.01); *G01N 33/54386* (2013.01); *G01N 33/551* (2013.01); *G01N 33/56927* (2013.01); *G01N 33/56983* (2013.01); *H01L 41/113* (2013.01); *H01L 41/253* (2013.01); *G01N 2291/0255* (2013.01); *G01N 2291/0256* (2013.01); *G01N 2291/0427* (2013.01)

(56) References Cited

U.S. PATENT DOCUMENTS

| | | | | |
|---|---|---|---|---|
| 4,242,096 | A | | 12/1980 | Oliveira et al. |
| 4,314,821 | A | | 2/1982 | Rice |
| 5,098,893 | A | | 3/1992 | Franks et al. |
| 5,130,257 | A | | 7/1992 | Baer et al. |
| 5,306,644 | A | * | 4/1994 | Myerholtz ........... G01N 29/022 310/311 |
| 5,350,961 | A | | 9/1994 | Chu |
| 5,527,711 | A | * | 6/1996 | Tom-Moy ............ C07D 495/04 205/778.5 |
| 5,658,732 | A | | 8/1997 | Ebersole ............... C12Q 1/6825 422/68.1 |
| 5,837,446 | A | | 11/1998 | Cozzette et al. |
| 6,235,488 | B1 | * | 5/2001 | Tom-Moy ............ G01N 29/022 422/504 |
| 6,582,969 | B1 | | 6/2003 | Wagner et al. |
| 6,723,516 | B1 | * | 4/2004 | Tom-Moy ............ G01N 29/036 422/82.01 |
| 7,135,295 | B1 | * | 11/2006 | Willner ................. C07K 16/00 427/2.11 |
| 7,148,611 | B1 | | 12/2006 | Liu |
| 7,267,993 | B2 | * | 9/2007 | Pentrenko ........ G01N 33/54373 435/4 |
| 8,136,403 | B2 | | 3/2012 | Seppa et al. |
| 2006/0024813 | A1 | | 2/2006 | Warthoe |
| 2009/0194507 | A1 | | 8/2009 | Cernak |
| 2010/0104476 | A1 | | 4/2010 | Ibanez et al. |
| 2011/0053139 | A1 | | 3/2011 | Larson et al. |
| 2011/0136262 | A1 | * | 6/2011 | Ragavan ............. G01N 29/022 436/518 |

FOREIGN PATENT DOCUMENTS

| | | |
|---|---|---|
| EP | 1804059 | 7/2007 |
| JP | H07-35669 | 2/1995 |
| JP | 2008-002959 | 1/2008 |
| JP | 2008002959 | 1/2008 |
| JP | 2010-151848 | 7/2010 |
| WO | WO 94/28417 | 12/1994 |
| WO | WO 01/29553 | 4/2001 |
| WO | WO 2010/007615 | 1/2010 |
| WO | WO 2010138871 | 12/2010 |

OTHER PUBLICATIONS

International Search Report for International Application No. PCT/US2012/052583 dated Nov. 12, 2013 (1 page).
Lange, et al., "Surface Acoustic Wave Biosensors: A Review," Analytical and Bioanalytical Chemistry, Feb. 12, 2008, vol. 391, pp. 1509-1519.
Gizeli et al., "Antibody Binding to a Functionalized Supported Lipid Layer: A Direct Acoustic Immunosensor", Analytical Chemistry, vol. 69, No. 23, Dec. 1, 1997, pp. 4808-4813.
Greg T. Hermanson, Bioconjugate Techniques, 1996, 2nd Edition 2008, Pierce Biotechnology Thermo Fisher Scientific, Rockford, Illinois, 2008 Elsevier Inc., Academic Press, ISBN: 978-0-12-370501-3, p. 142.
Tsortos et al., "Quantitative Determination of Size and Shape of Surface-Bound DNA Using an Acoustic Wave Sensor", Biophysical Journal, vol. 94, Apr. 2008, pp. 2706-2715.
Richard T. Pon, "A Long Chain Biotin Phosphoramidite Reagent for the Automated Synthesis of 5'-Biotinylated Oligonucleotides", Tetrahedron Letters, vol. 32, Issue 14, Apr. 1, 1991. pp. 1715-1718.
Andle et al., "Selective Acoustic Plate Mode DNA Sensor", Sensors and Actuators B Chemical, 24(1):129-133, Mar. 1995, Abstract only.

* cited by examiner

A                                      B

C

A

B

A

B

C

Panel A

- Contact Points
- IDT Wave Generator
- IDT Wave Receiver
- Fluid Chamber
- Inlet Port
- Filter
- Antibody
- Antigen
- Outlet Port
- Biosensor Cartridge Panel B

BIOCOATED PIEZOELECTRIC BIOSENSOR PLATFORM FOR POINT-OF-CARE DIAGNOSTIC USE

This application is being filed on 26 Feb. 2014, as a U.S. National Stage of PCT International Patent application No. PCT/US2012/052583, filed 27 Aug. 2012 in the name of Aviana Molecular Technologies, LLC, a U.S. national corporation, applicant for the designation of all countries except the US, Lisa Laury-Kleintop, a citizen of the U.S., Hsu-Cheng Ou, a citizen of Taiwan, and Herman Rutner, a citizen of the U.S., applicants for the designation of the US only, and claims priority to U.S. Provisional Patent Application Ser. No. 61/527,716, filed Aug. 26, 2011. and which applications are incorporated herein by reference. To the extent appropriate, a claim of priority is made to each of the above disclosed applications.

FIELD OF THE INVENTION

The present invention relates generally to devices and methods for analyzing test samples containing target analytes including proteins and nucleic acids. The invention uses integrated chips as sensitive biosensors having a biocoating with the ability to irreversibly bind an avidin or another protein/nucleotide onto piezoelectric material (e.g., crystal) surfaces. The resulting platform technology is suitable for the development of a variety of biosensors. In more specific embodiments, the biocoating is applied directly onto the piezoelectric material surface without intervening coatings. In another specific embodiment, the present invention relates to an acoustic plate mode biosensor, where interdigitated transducers (IDT's) are present on a surface opposite side from the one bearing the biocoated film, obviating the need for protective coatings and waveguides on the crystal.

BACKGROUND OF THE INVENTION

Low cost, mass produced point of care (POC) biosensors with sensitive, specific and rapid detection technologies have potentially enormous epidemiological impact on global human and veterinary health. No other societal need would benefit from suitable devices as much as the timely detection and treatment of infectious diseases, especially acute ones, often of epidemic proportions, affecting humans and animals. Suitable POC devices would have to be manufactured at a low cost and in large quantities to allow monitoring of large populations of potentially exposed individuals. These sensors need to be robust enough to be used in adverse conditions such as tropical and subtropical climates and also be simple to use by non-laboratory trained personnel in both resource rich and resource limited setting. In addition, such devices should be single-use, low cost and disposable so as not to be a transmitter of disease. Current state of art POC devices, like lateral flow devices, do not meet this need, because of low sensitivity and/or high variability of results, among other flaws. On the other hand, highly sensitive diagnostic tools such as nucleotide detection require sophisticated separation and processing, making these diagnostic devices difficult in field settings. The laboratory based systems are accurate (both sensitive and specific), but they are not easily transportable or rapid and they require specially trained personnel to operate them. The present invention describes a process that results in a highly sensitive biosensor which can be used as a POC device in any number of settings. These biosensors provide a scalable biocoating on known (as well as on innovative) acoustic wave sensors, making the sensors used in a variety of non-biological settings available for use in POC devices in non-laboratory, e.g., field, settings.

Acoustic waves generated in piezoelectric crystals are well known to be extremely sensitive when applied to the device due to mass and/or viscosity changes, resulting in a change in the frequency and/or phase or amplitude of such acoustic waves before and after application of the mass, which can be electronically measured and correlated to presence of the mass. Hence, they are used as very sensitive chemical or gaseous sensors with the ability to detect mass changes in parts per billion or very small changes in temperature or changes in gas concentrations. However, the use of these devices as biosensors, made from piezoelectrically active materials such as crystals has had limited success either because the applied biological fluid suppresses the generated wave or because the applied films are difficult to manufacture consistently on a large scale, limiting them to resource-rich, sophisticated settings such as research laboratories.

Attempts at functionalizing these acoustic wave sensors as biosensors have resulted in tedious or inconsistent and difficult-to-scale-up processes. In addition, these coating processes must also take into consideration the electrical conductive units attached to these crystals to transmit the acoustic waves and in particular, must not interfere with wave transmission. (Similarly, the crystal structure must be compatible with wave transmission.) Furthermore, the biocoating processes must not attenuate or destroy the acoustic waves. Given these various limitations, progress on biocoating has consistently used a similar approach—namely to attach a chemical agent to the crystal surface which can also bind bioactive agents such as antibodies etc. Two methods are commonly used for depositing the first functional coating: one involves applying a thin layer of vacuum sputtered gold that is reactive with the sulfur function on heterobifunctional thiols or derived disulfides (such as carboxymethyl-Peg-thiol, 5000, Laysan Bio) and the other involves direct functionalization of hydroxyl groups on piezoelectric sensor surfaces with a suitable commercially available heterobifunctional silane, e.g. 3-aminopropyl triethoxysilane (APTES), 3-glycidoxypropyl triethoxysilane (GOPS), 3-mercaptopropyl triethoxysilane (MPTS), to form covalent mono or divalent silicate bonds with the silanes. Another avidin affixation method involves first the deposition of lipids (Annals of Chem. Vol 69:4808-4813) and hydrogels onto a surface acoustic wave sensor (Australian Patent 07473551) followed by deposition of avidin.

These methods are often time consuming and the processes for coating complex. They require prolonged liquid phase contact with a heterobifunctional silane reagent. These silanes are generally provided as solutions in non-reactive solvents like toluene, 2-propanol, or in an aqueous solvents, etc. to deposit mono or multilayers. However, this process is difficult to control for several reasons. First, some of the silanes, such as trimethoxysilanes are very reactive; others, like triethoxysilanes, are less reactive but hydrolytically less stable. Another reason is that because of the reactivity of silanes, their possession of several linkable groups and their tendency to react and link up with additional silane molecules, it is difficult to achieve a single layer of silane deposit which changes the transmission properties of the coated substrate in a manner difficult to control and maintain uniform. The presence of even trace amounts of water additionally complicates process control because the silanes become even more prone to crosslinking by forming reactive silanols or silanediols. The commonly used APTES is particularly prone to multilayer formation. The heterobifunctional silane, GOPS, bears an epoxy or oxirane group that is selectively reactive with thiols, amines and hydroxyl groups, primarily depending on pH, e.g. with thiols at pH of about 7, with amino groups at pH about 9, and with hydroxyl groups at pH>10. It can be used for direct conjugation to one or more amino groups on antibodies or to about half the amino groups on immobilized avidin, such as neutravidin. But these procedures involve wet chemistries and covalent bonds which complicate and delay the coating process and raise the possibility of side reactions, which would interfere with accuracy of the resulting device. (G T Hermanson in Bioconjugate Techniques, 1996, page 142).

In summary, the prior art SAM processes for depositing the intermediary and final protein layer on a piezoelectric material require sequential steps, comprising incubations with multiple reagents in aqueous solvents or inert aprotic media, intermediate rinses, pH changes and final exposure to the binding protein to complete the desired functional SAM affinity biosensor. These stepwise processes may take hours or even several days and may yield SAM biosensors that are functionally variable, expensive and thus unacceptable for POC biosensor applications. Such processes in the art are clearly not suitable for consistent and cost-effective manufacturing of uniform biosensors at low cost and in a scalable high-throughput mode of potentially millions of single use biosensors where process variations or failure would be highly undesirable.

The invention describes, in part, a process which allows direct binding of proteins such as, not only avidins but also other biological materials (nucleic acids, other proteins) having the requisite linkable groups directly on the crystal surface resulting in stable, scalable processes for making uniform, reliable biosensors. The present invention further incorporates the use of both types of sensors, namely, bulk waves and shear horizontal surface acoustic waves and can be used on a number of piezoelectrically active crystal materials. Using this direct coating, the present invention has overcome many of the difficulties mentioned above.

While piezoelectric materials used to create acoustic wave guides are well known and comprise lithium niobate, lithium tantalite, quartz and a few other stances, each provide unique advantages and disadvantages in developing a platform device. Accordingly, it is desirable that any coating method be applicable to all piezoelectric material substrates in order to provide the largest potential variations for detecting the varied and multiple agents in nature responsible for causing infections and their consequences, including but not limited to bacteria, viruses, proteins, nucleotides, parasites, fungus, among others, and notably both individual components thereof and larger particulates such as fragments of pathogens.

SUMMARY OF THE INVENTION

An acoustic wave biosensor system is described that incorporates a biofilm deposited on the sensor surface of a piezoelectric medium (crystal). The biofilm includes a coating of bioactive anchor substances for which a specific binding partner exists, such as avidins (but also other proteins such as ligands and nucleic acids such as oligo and poly nucleotides having specific binding partners can be used), forming a stable monolayer directly onto crystal surfaces. The process is adapted for scale up to large scale manufacturing using automated or semi-automated techniques.

Accordingly, the present invention is directed to a biosensor comprising a piezoelectric medium having an anchor layer, such as an avidin film) coated directly on the piezoelectric surface and to methods for its manufacture and use. In the case of an avidin coating, in order to detect target analytes in a biological sample, a biotinylated capture reagent is bound to the biofilm. In the case of other anchor substances, the capture reagent must be derivatized with a specific binding partner for the anchor substance. A biological sample containing the target analyte is placed in contact with the biofilm. The capture reagent specifically recognizes and binds to the target analyte. The binding is detected as a perturbation (change in frequency, phase, and/or amplitude) of an acoustic wave traversing the sensor surface. This perturbation is then converted to an electronic signal for further analysis, namely correlation with the presence of the target analyte and, optionally, quantification of same.

In a further aspect, the biosensor substratum can be modified with an intermediary substrate layer of silica, zirconia, titania and the like, not as done conventionally by costly and tedious thermal vacuum sputtering methods, but by a simple two-step process of covalent bonding of silicate, titanate, zirconate and the like, by contact of the respective salt in a suitable medium with a bare piezoelectric chip substratum surface under controlled conditions, followed by conversion of the bound substrate layer to a layer of silica, titania, zirconia and the like by means of an acid treatment step, thereby forming a uniform secondary oxide layer of controllable thickness, depending on salt concentration and contact time, wherein such intermediary oxide layer (or layers) can subsequently be coated with a stably bonded anchor layer (such as an avidin) that is suitable for reaction with a specific capture reagent (such as an antibody to a specific analyte target) suitably modified with a specific binding partner to the anchoring material (such as a biotin group).

In yet another aspect of a biosensor comprising intermediary coating with a silicate, titanate, zirconate salt and the like, the coating solutions at optimal concentrations and pH can optionally be mixed with an alkali-stable avidin and allowed to dry, thereby both bonding the salt to the substratum layer and concurrently partially embedding the avidin in a glass like bonded salt film, which after acid treatment converts the bonded salt film to a porous oxide layer stably encapsulating the avidin which still has a substantial number of exposed biotin sites available for binding of biotinylated capture reagents.

In yet other aspects, the present invention is directed to a method of coating a biosensor adapted for the detection of one or more analytes in a biological sample using acoustic waves, the biosensor comprising a piezoelectric material with an anchor layer, such as an avidin layer, affixed to it, the method comprising depositing avidin onto a portion of one surface of the piezoelectric material, said portion adapted to receive the biological sample and securing the affixation of said avidin, directly or indirectly, onto said piezoelectric surface portion by a step comprising coating by methods herein disclosed.

The present invention further comprises the use of the novel piezoelectric biosensor devices and platform in a system for rapid POC diagnosis. Accordingly, the biosensor of the present invention provides the basis for a sensitive, inexpensive and easy method and associated device as a POC diagnostic tool. The present invention allows for a simple manufacturing process using novel rapid coating methods on existing manufacturing facilities or conveyor belts, resulting in novel single-use, potentially disposable biosensors which can be used as a cost-effective point of care (POC) alternative in clinical diagnosis. Such a biosensor can provide the needed sensitivity, can be deployed rapidly when needed and would thus be useful in both the developed world and in resource limited countries. In particular these POC biosensors can be especially beneficial in the areas related to the detection, containment and treatment of acute infectious diseases affecting humans and animals and detection of specific biochemical markers useful in diagnosis and monitoring of diseased and healthy patients.

An acoustic wave biosensor component comprising a piezoelectric crystal comprising a layer of an anchor substance directly bound to a surface of the piezoelectric material, the anchor substance having the property of binding to a capture reagent comprising or constituting a specific binding partner for the anchor substance.

A process for coating the surface of a piezoelectric material with biofilm comprising an anchor substance having the property of binding to a capture reagent comprising or constituting a specific binding partner for the anchor substance, the process comprising:

a. treating a crystal surface of a piezoelectric material to increase the surface energy of the crystal surface;
b. applying a layer of the anchor substance to the crystal surface;
c. to form a chemisorbed anchor layer on the crystal surface.

A process for coating the surface of a piezoelectric material with biofilm comprising an anchor substance having the property of binding to a capture reagent comprising or constituting a specific binding partner for the anchor substance, the process comprising:

a. applying to the crystal surface of a piezoelectric material a solution of a silicate, zirconate or titanate salt and reacting with an acid to form an intermediary layer respectively of silica, zirconia, or titania;
b. applying a layer of the anchor substance to the intermediary layer to form an anchor layer on the crystal surface.

An acoustic wave biosensor comprising:

a. a piezoelectric crystal comprising a layer of an anchor substance directly bound to a surface of the piezoelectric crystal, the anchor substance in the layer being also bound to a capture reagent the capture reagent comprising or constituting a specific binding partner for the anchor substance and specifically recognizing an analyte present in a biological fluid;
b. an acoustic wave generator, the generator generating a wave wherein a reaction between the capture reagent and an analyte causes a detectable change in properties of the acoustic wave.

A method for determining the presence or quantity of an analyte in a biological fluid sample the method comprising:

contacting the foregoing biosensor component with a composition comprising a capture reagent the capture reagent comprising or constituting a specific binding partner for the anchor substance and also specifically recognizing an analyte;

causing the capture reagent to bind to the anchor substance, forming a capture reagent layer;

contacting the bound capture reagent layer with a biological fluid sample;

and generating an acoustic wave across the piezoelectric surface; and measuring any change in amplitude, phase or frequency of the ware result of analyte binding to the capture reagent layer.

BRIEF DESCRIPTION OF THE DRAWINGS

FIG. 1: Atomic Force Microscopy (AFM) of neutravidin coating on lithium niobate crystal. AFM image analysis showed a neutravidin coating approximately 3 nm to 4 nm using the process described in Example 1. Panel (a) shows the real time topography graph of chips with no neutravidin bound. Panel (b) shows a 10 μm scan of the neutravidin coated surface having a 1 μm nanoindented area. Panel (c) is a topography graph of avidin bound to the chip after indentation having a depth of approximately 3.229 nm.

FIG. 2: Atomic Force Microscopy of neutravidin coating on lithium niobate crystal with added anti-dengue antibody. Neutravidin bound to the lithium niobate chip with the addition of anti-dengue antibody. Panel (a) shows a 10 μm scan of the nanoindented area made in the neutravidin with Ab surface by scanning a 1 μm area of the chip. Panel (b) shows a 4.6 μm magnified portion of Panel (a). Panel (c) is a topography graph showing the depth to be 0.269 nm (or 6-9 nm in depth).

FIG. 3: FITC-labeled biotin beads used to confirm avidin on the surface of the lithium niobate chip. Fluorescent image (200×) of biotin beads (Invitrogen) is shown without (a) or with (b) avidin on the surface of the lithium niobate chip. Arrow in (a) indicates non-specific binding of beads to crystal. Arrow in (b) indicates binding of beads to avidin coating on crystal.

FIG. 4: Stability of avidin binding. The optical density (O.D.) of Avidin bound to lithium niobate was determined over a 1-month period. Avidin-coated chips were stored at 4° C. and tested each week. The binding remained approximately the same for weeks 1, 2, and 4 (the decline in week 3 was not considered valid and was attributed to faulty reagents).

FIG. 5: Avidin binding to lithium niobate. Avidin was bound to $SiO_2$ coated onto lithium niobate using methods described. Panel A shows the optical density (O.D.) of avidin bound to silicon dioxide coated on lithium niobate. The absorption values at 490 nm for Biotin HRP with and without avidin were compared. The graph shows good binding of avidin with a difference in O.D. reading of 1.4. Panel B compares neutravidin to avidin binding on silicon dioxide coated on lithium niobate.

FIG. 6: Fluorescent microscope image of AMT chip binding to the elementary bodies (EB) of *Chlamydia trachomatis*. Shown are fluorescence images of the AMT chip having bound EB with DAPI stain (Panel B—arrows) and the FITC-labeled anti-*C trachomatis* Ab (Panel C—arrows) compared to negative control without *chlamydia* material (Section A). The presence of DAPI and FITC-label confirmed the bound material was cellular (DAPI) and was *chlamydia* (FITC).

FIG. 7: Frequency shift with *chlamydia* and anti-*chlamydia* antibodies. A frequency shift from a stabilized baseline is shown on a chip prepared with avidin according to the procedure of the present invention after the addition of $10^5$ EB with 0.25 μg/ml biotinylated Anti-EB LPS.

FIG. 8: Frequency shift with the addition of dengue virus. A frequency shift from a stabilized baseline is shown on a chip prepared with avidin and 4 μg/ml of anti-dengue type 2 according to the procedure of the present invention. A change in the baseline frequency occurs with the addition of 8 μg/ml dengue virus.

FIG. 9: Frequency shift with the addition of antibody alone to a chip bound to only neutravidin. A frequency shift of 4.5 MHz between arrows 1 and 2 are shown when a 1:200 dilution of biotinylated anti-*chlamydia trachomatis* (MOMP) was added to a chip having bound avidin.

Figure 10:
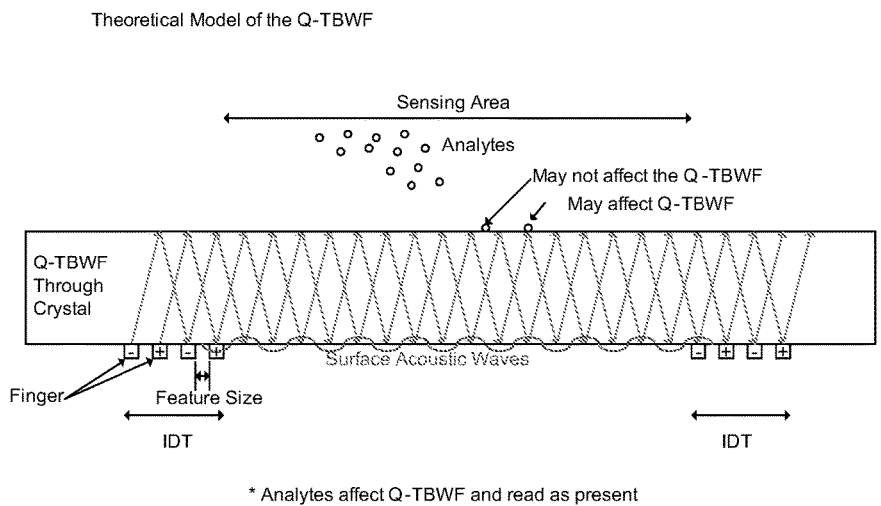

FIG. 10: Theoretical model for acoustic plate mode (APM). A theoretical model of the APM used in the present invention (APM is designated as Q-TBWF). The sensing area corresponds to the fluid chamber where the biological sample is placed at the top of the piezoelectric substrate. The wave is generated at the bottom and moves through the piezoelectric medium to detect the analyte bound to the top surface (via an avidin molecule affixed directly to the surface). IDTs are at the bottom surface (not shown). Upon encountering the extra mass of the captured analyte, the frequency of the wave will change.

Figure 11A:
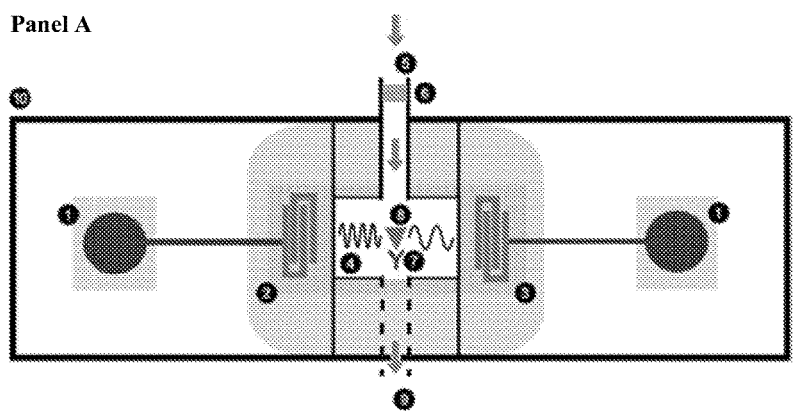
Figure 11B:
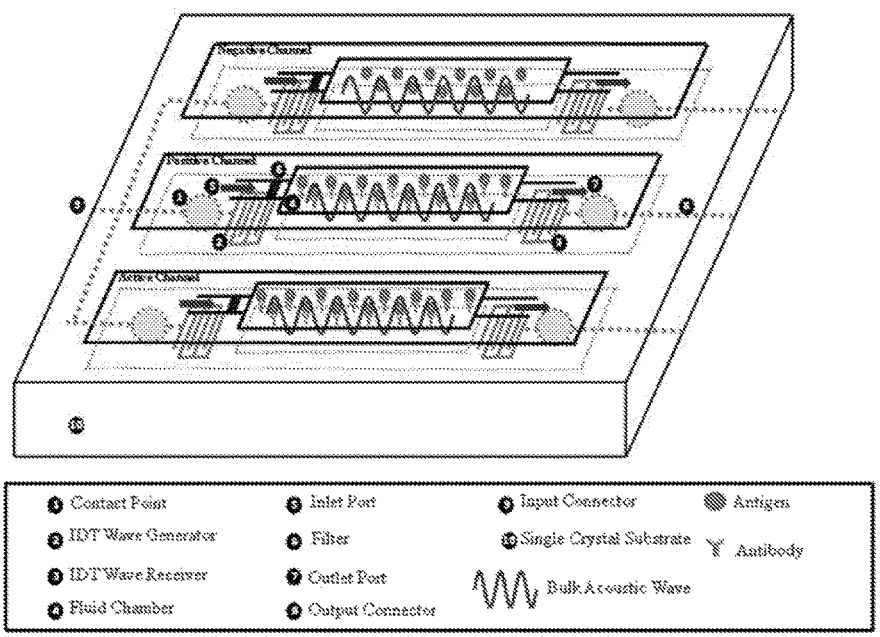

FIGS. 11A-11B: Schematic of an integrated multi-array device. A schematic design of the device is shown having a single delay line structure with the APM mode. In the APM mode, the electronic elements (e.g., IDTs) are applied to the substrate on the side opposite of the side in contact with the biological and fluidic elements. FIG. 11A is a top perspective view of the device having a single delay line structure. FIG. 11B is a top side perspective view with three delay lines (multichannel chip).

DETAILED DESCRIPTION OF THE INVENTION

Definitions

The following terms shall have the meaning ascribed to them below.

"Anchor substance" denotes a coating material that binds both to (i) the piezoelectric crystal (for "direct" binding) or to an intermediary coating thereon and (ii) to a "capture reagent" (as defined below). The term includes avidins, a member of a family of proteins functionally defined by their ability to bind biotins, which serve as their specific binding partners (examples, avidin, streptavidin, neutravidin), as well as oligo and polynucleotides and proteins having a specific binding partner which could be used to modify a capture reagent and therefore to cause the capture reagent to bind to the anchor—coated piezoelectric material. Also included are naturally occurring carbohydrate-binding lectins, which bind to carbohydrate groups e.g., on antibodies and antibody fragments (e.g. Fc fragments). Generally it is not preferred to use a capture reagent as an anchor because of the risk of changing the conformation or even partially denaturing the capture reagent which would affect accuracy of the test. Oligo and polynucleotides can bind to piezoelectric materials through ionic or dipole sites, either directly or through intermediary silver coating applied, e.g., by ion exchange methods. Their specific binding partners are complementary nucleotide molecule and those can be used to modify capture reagents.

"Capture reagent" means a substance that specifically binds to an analyte in a biological sample, such that it can be used to identify and/or quantitate the analyte by capturing it from the biological sample. The term includes antibodies, aptamers and fragments thereof without limitation. A capture reagent will bind to the anchor substance with or without modification with a linking group which is a specific binding partner for the anchor substance (e.g., biotinylation or complementary nucleic acid). In other words, the capture reagent is or comprises a specific binding partner for the anchor substance and simultaneously specifically recognizes an analyte.

"Direct" or "directly" as applied to binding of an anchor substance to a piezoelectric surface means binding to the piezoelectric crystal without application of an intermediary coating thereon. The piezoelectric surface may be modified, for example by application of plasma, ultraviolet radiation, or by ion exchange deposition of silver ions, which replace metal ions on the surface but do not deposit an additional layer of intermediary material on the surface metal ions on the piezoelectric surface. Excluded are intermediary coatings such as those resulting from silane treatment, or any other reaction forming covalent bonds or gold, silver or copper layer deposition.

Biofilms previously exploited in the prior art are inadequate and not adaptable to the manufacture of low cost, single use biosensors, especially with respect to the large quantities needed for screening potentially large populations. Typical examples include the use of silanes (US Patent Publication No. 2011/0053139) or hydrogels (US Patent Publication No. 2006/0024813). The present invention describes a new type of biofilm, a process for applying it to a substrate, and the use of this biofilm in biosensors that incorporate any one of several modes of acoustic waves, along with the application of these biosensors in diagnostic POC and biomedical research. The application of the biofilm includes coating proteins that are conjugable with a binding partner directly onto crystal surfaces in a stable monolayer which is simple to scale up to large scale manufacturing. The base biofilm can be adapted to several modes of acoustic waves and can be used in multi-array microsensors for running several tests in parallel. In addition, the coating can be applied to a number of piezoelectric materials such as lithium niobate, lithium tantalite and quartz microcrystals, among others. Acoustic waves are described by the mode of wave propagation through or on a piezoelectric substrate. Many combinations are possible, depending on the material and boundary conditions. The interdigitated transducer (IDT) for each sensor provides the electrical activating field, the input transducer provides the electrical input that propagates the wave in the crystal which is based on the crystal cut and placement of the transducer. Any change on the crystal that results in a change to the wave is read by the output transducer and conveyed to a processor for analysis.

The present invention further describes a new application for an acoustic plate mode.

1. Biocoating Methods

The present invention describes a new biocoating process that is applicable to all types of acoustic waves and all types of piezo materials used in the manufacture of acoustic wave sensors. One embodiment includes their use in bulk modes, where the IDTs are positioned on the piezo material surface opposite from that where the biofilm is deposited. Suitable acoustic waves can include all bulk modes, acoustic plate modes and shear-horizontal plate modes. In another embodiment, a related biocoating can be used as an acoustic wave guide for surface and shear horizontal modes, which dispenses with the requirement of having IDTs and biocoating on opposite piezo surfaces.

A. Direct Coating: The coating involves simple and rapid coating chemistries that are executed in seconds or minutes rather than hours; manufactured using a scalable, continuous and in-line method; easily automated with minimal operator intervention; produces a low number of rejects; and generates small amounts of hazardous waste. This coating method deposits anchor substances directly on the piezoelectric surface without an intermediary layer of material.

Avidins are proteins derived from egg whites, e.g., from avian reptile and amphibian species, and have been used in many biochemical reactions. The avidin family includes neutravidin, streptavidin and avidin, all proteins functionally defined by their ability to bind biotin with high affinity and specificity. Avidins can also include bacterial avidins such as streptavidin and modified avidins like neutravidin (deglycosylated avidin from Thermo Scientific—www.thermoscientific.com). They are small oligomeric proteins, each comprising four (or two) identical subunits, each subunit bearing a single binding site for biotin. When bound to the surface of the biosensor in the present invention, two sites are facing the piezo material surface, and are hence unavailable for biotin binding. The remaining two sites are facing away from the piezo material and are available for biotin binding. The binding affinity of avidins to biotin, albeit noncovalent, is so high that it can be considered irreversible. The dissociation constant of avidin ($K_D$) is approximately $10^{-15}$ M, making it one of the strongest known non-covalent bonds. In its tetrameric form, avidin is estimated to be between 66 to 69 kDa in size. Ten percent of the molecular weight is attributed to carbohydrate content composed of four to five mannose and three N-acetylglucosamine residues. The carbohydrate moieties of avidin contain at least three unique oligosaccharide structural types that are similar in structure and composition.

Biotin, also known as d-biotin or Vitamin H, Vitamin B7 and Coenzyme R, is a specific binding partner of avidin. It is commercially available from multiple suppliers, including Sigma-Aldrich.

The present inventors discovered that direct coating of anchor substances, such as avidins, onto a piezoelectric material, including all actively piezoelectric materials, can be obtained under the conditions discussed herein. Using this process, anchor substances are successfully attached directly to a piezoelectric crystal surface and form a strong and stable non covalent bond, preferably in a monolayer. As shown in FIG. 1, Panels B and C, in one embodiment, avidins form a monolayer of about 3-4 nanometers on a lithium niobate chip. Using Atomic Force Microscopy (AFM), the single largely uniform monolayer was determined as expected for a "pancaked" chemisorbed avidin. The AFM measurements involves an extensive two hour wash in PBS and then in distilled water, and a neutravidin coated chip is then imaged. Panel A shows a real time topography graph of a blank chip with no neutravidin bound to the chip. Panel B is a 10 µm scan of an area on an avidin coated chip having a 1 µm nanoindented portion. The Z-value is defined as the distance from the top of the Avidin on the chip surface to the highest peak. As determined from the topography graph in Panel C for a typical indentation created in Avidin bound to the crystal, the depth was 3.229 nm. The indentations were determined to be in a range of 3 to 4 nm in depth. A typical neutravidin size is approximately 5.6×5×4 nm (Biophys J. 2008 Apr. 1; 94(7): 2706-2715. Published online 2008 January 10.1529/biophysj.107.119271, A Quantitative Determination of Size and Shape of Surface-bound DNA Using an Acoustic Wave Sensor, Tsortos, et al. PMCID: PMC2267124). To assess the neutravidin layer depth, an indentation is made in one spot and rescanned. The indentation means permits to calculate the depth of avidin bound to the surface. The monolayer height is measured from the top of the indentation to the floor of the indentation. In the uncoated chip, the indentation does not result in any depth change. Both scans are done within a 10 micrometer space.

Figure 2:
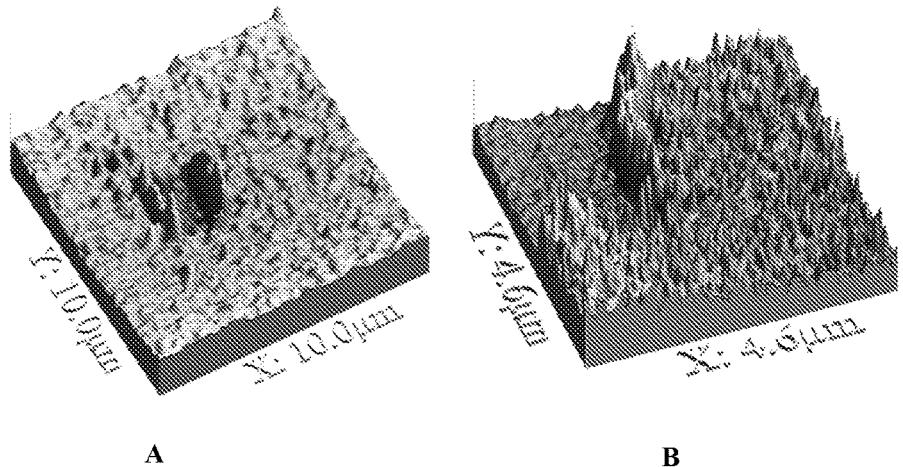
Figure 2:
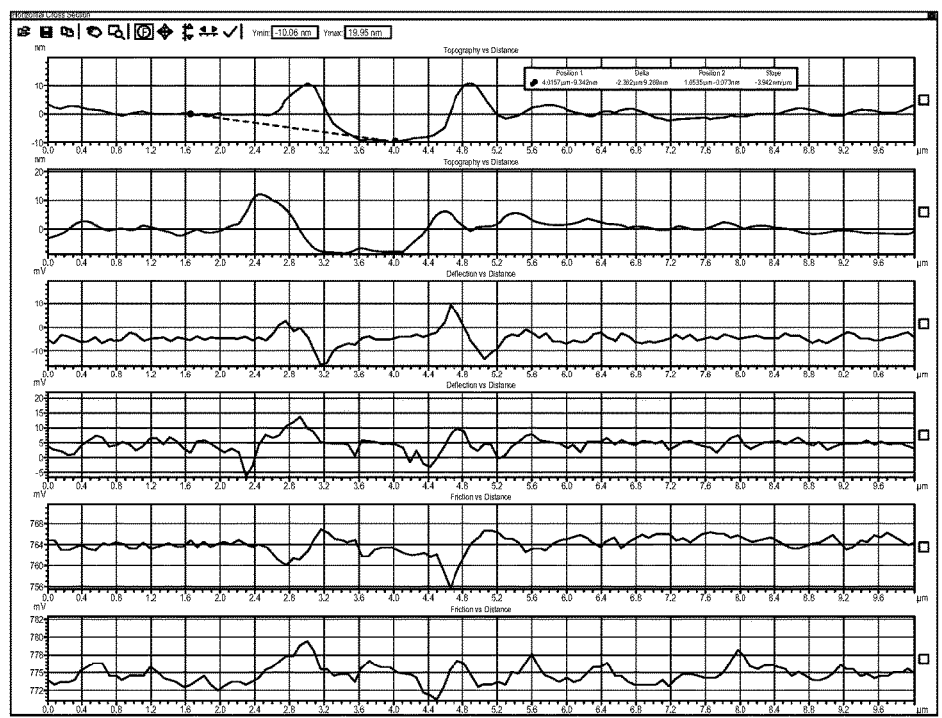

FIG. 2 illustrates the incorporation of biotinylated antidengue antibody onto a neutravidin coated lithium niobate crystal. Avidin was bound to the lithium niobate chip using the methods of the present invention, then 4 µg/ml of biotinylated anti-dengue antibody in 0.05% BSA-PBS was applied for 30 min at room temperature. After extensive 2-hour wash in PBS followed by a distilled water rinse, the chip was submerged into distilled water and imaged using AFM. Panel A shows a 10 µm scan of the nanoindented area made in the avidin with bound antibody. Panel B is a 4.6 µm magnified portion of Panel A. The indentation is shown to be 6-9 nm in depth, as shown in the topography graph in Panel C. The depth is 9.269 nm. The depth was measured from the top of the avidin on the chip to the bottom of the 'hole' or top of the chip itself. Given the dimensions of an antibody 14.2 nm×8.5 nm×3.8 nm, the depth of the indentation shows that the antibody bound to the avidin.

Without being limited to a particular theory, it is believed that the strength of this binding is due to the exposure conditions discussed below, resulting in strong non covalent bonding of the anchor substance (e.g., avidin) to the crystal surface. It is probable that this binding is taking place through some of the side chains of reactive amino acids on the avidins like arginine, cysteine and lysine which form a link to the crystal surfaces. Other side chains that can form bonds, with the piezoelectric surface, are on the uncharged and charged polar amino acids (for example, uncharged-serine, threonine, asparagine, glutamine, tyrosine; charged-aspartic acid, glutamic acid, arginine, histidine). When oligo or polynucleotides are used as an anchor substance, they bind through ionic or dipole sites and once immobilized they bind to capture reagents which can be or can be modified with complementary oligo or polynucleotides. Indeed, if the analyte is nucleic acid, the capture reagent can be a hybrid oligo or polynucleotide that binds the anchor reagent at one moiety and the analyte at the other moiety.

Prior to coating, plasma treatment removes virtually all organic contaminants on the surface of the crystal via the generation of highly reactive species. There are two mechanisms believed to help attach the anchor substance to the crystal surface: plasma treatment induces higher surface energy which allows better wetting for the fluid/liquid applied leading to better contact between the crystal and anchor substance and it introduces functional groups such as amine, carboxyl and hydroxyl on the surface thus providing interfacial adhesion via bonding. Regardless of the mechanism, coating of the anchor on the crystal surface is achieved in some embodiments without an intermediary coating and in any event without. covalent bonds which require wet chemistries. The bonds thus formed are believed to be due to chemisorption which is a more tenacious form of attachment than physisorption.

It is further believed that the resulting potential bond between reactive groups on the anchor substance and reactive species on the crystal are all possibly involved on a multipoint interaction, each weak, but collectively working to increase exponentially to strong bonding by a "zipper" or "velcro" effect as also seen in the weak binding of base pairs in DNA strands that are difficult to break except under severe thermal conditions. These conditions will not be applied to biosensors, since there is a need to protect the antibodies used in this reaction from denaturation and/or conformational change detrimental to accuracy of the test.

In some embodiments prior to coating sensors with an anchor substance such as avidin, the following steps are performed. Individual chips are made from piezoelectric wafers and are using conventional microlithography. IDT may be secured on the opposite side of the coated chip by mounting the IDT side inside the lower part of the cartridge housing. The crystal surface first has to be well cleaned of all organic substances by cleaning the surface using for example a plasma treatment that may include, for example, an exposure to an atmospheric plasma generated jet stream, (Plasma Treat Co.). Alternatively or in addition, an ultraviolet-ozone treatment can be applied. The anchor layer (usually 5-10 seconds), avidin, is applied in a suitable solvent by spraying or contact transfer (e.g., by a process resembling printing, such as ink jetting or roller application) to form a thin uniform liquid film or microdot pattern. The amount of anchor substance in the film should be calculated to form a monolayer. Of course the exact amount will depend on the choice of anchor substance and on if affinity for the piezoelectric surface. A generally useful range for the anchor substance is 0.01 mg/ml to 5 mg/ml; in some embodiments, 0.01 to 2 mg/ml has been found to be a workable range; with some embodiments further narrowing the range to 0.01 mg/ml-1.0 mg/ml. The next step comprises rapid drying with a stream of heated air, resulting in a stable layer of avidin as the first binder layer. The resulting sensor is generic in the sense that it can be further modified with any desired capture reagent specifically recognizing a particular analyte or it can be reacted with a capture reagent already exposed to and bound to analyte. In this generic state it can be sealed (preferably in an $N_2$ atmosphere) and stored until needed.

One embodiment comprises a reagent composition containing neutravidin: 0.05 to 5 mg/ml in water, applied as a thin layer with less than 10 µl fluid per 0.5×1 cm piezoelectric material surface (about 3-10 µl of fluid/0.5 $cm^2$ and preferably 5-10 µl). Biotinylated capture reagents are prepared using conventional biotinylation reagents and related methods (Invitrogen). The degree of substitution is typically 3 to 5 biotins per capture reagent, typically IgG but nucleic acid or any other protein capture reagents can in principle be used. The concentrations in coating buffers are optimized for specific requirements needed in capturing different target antigens as defined in the examples but such action is within the skill of the art.

An example for a coating buffer for biotinylated capture reagent: 0.01M PBS buffer which may also contain a sugar, such as 1-10% trehalose or sucrose, and 5-10% purified glycerol. The sugar and glycerol function as preservatives and encapsulating agents. Sodium azide (0.01 to 0.05%) is added as an antimicrobial but another such agent can be used instead.

Figure 3:
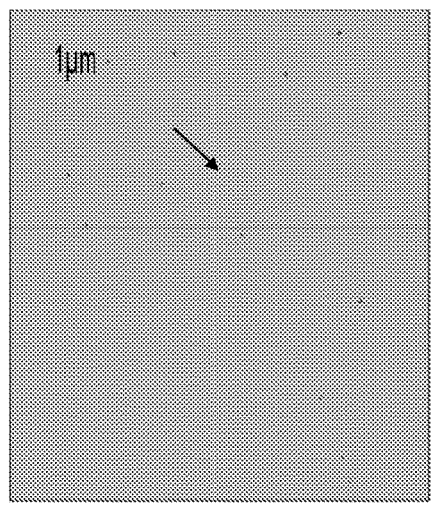
Figure 3:
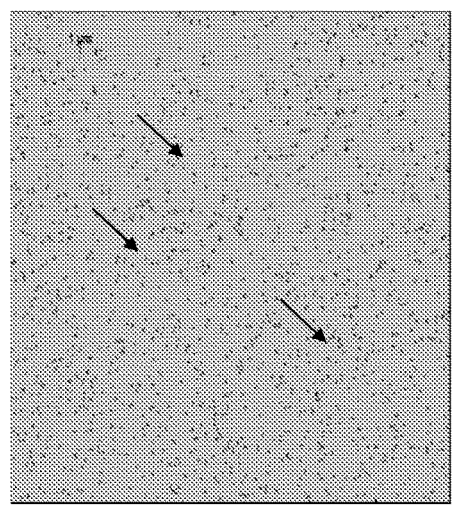

FIG. 3 shows confirmation of the specific binding of biotinylated fluorescent latex beads (FITC loaded, 1.1 µm, from InVitrogen) when imaged on a fluorescence microscope. In the confirmation, 0.25 mg/ml of avidin was bound to lithium niobate using the method as described above. After extensive PBS and deionized water washes a volume of 1 µm FITC labeled biotin beads (Invitrogen) containing 10,000 beads per ul of were added to the chip and incubated for 30 minutes at RT. After another wash with water, the chips were imaged under a fluorescent microscope (200×). The arrow in Panel A is trace of non-specific binding (see arrow) while the arrows in Panel B are representative of the specific binding of the beads. The bound beads were resistant to hydrodynamic or flow stresses up to several pN using gentle washing with buffers containing Tween 20, hence they are sufficiently stably bonded to multiple immobilized avidin on the niobate surface for purposes of uses of the sensor of the invention.

The stability of the avidin coating of the biosensors is surprising and is attributed to a chemisorptive process which is more tenacious than physisorption. Physisorptive binding was found to be easily removed by buffers and reagents and susceptible to thermal damage, especially when stored at elevated temperatures above 50° C. Thus the chemisorption process provides an improved low cost generic biosensor when used in combination with capture reagents for capture and detection of specific target entities.

Accordingly, the coating processes as described in the present invention are able to rapidly form thermally stable monolayers of anchor substance thereby providing a storable generic biosensor chip using a simple low cost process with potentially better long term stability than prior biosensors also bearing biotinylated antibody. When avidin coated chips made using this process were already examined under Atomic Force Microscopy, a single largely uniform monolayer of 3-4 nanometers was observed. See FIG. 2A.

The present invention further considers complete monolayers forming coatings with controllable surface densities, wherein surface densities are defined as the number of molecules occupying the biosensor surface as a complete monolayer carpet. The molecular parking areas are given in nm squared per molecule. Therefore when the total surface area of the biosensor is known, the number of deposited molecules on the full biosensor surface of known surface area can be determined, and the concentration of anchor substance in the coating solution can be adjusted to yield the desired monolayer. Fixed or unfixed mono or sub monolayers are preferred to multilayers which have lesser stability during washings or in their capture reagent bearing layer. This is especially relevant when using wash fluids containing surfactants, e.g., Tween 20 or saponin.

B. Stability of the Coated Biosensor: Once applied, the stable anchor layer is optionally further stabilized by cross-linking with a reversible cross-linking agent such as formaldehyde vapor, although other homobifunctional cross-linking agents such as glyoxal, or glutaraldehyde can be used, Crosslinking is accomplished with up to 24 hours exposure to phosphate buffer (10%) or brief solvent fixation with methanol, isopropanol or acetone as done in standard tissue histochemistry. Over cross-linking is avoided by following the suggested time and concentrations as stated in the supplier's instructions, so that the 2 or 3 remaining exposed biotin binding sites on avidin are not affected. Optionally, the binding sites can be protected from collapse by prior exposure to reversibly bound desthiobiotin (Sigma) which is then easily displaced by biotin or biotinylated capture reagents. This may also be followed by thermal fixation at temperatures of up to 70° C. for several minutes as certain anchor substances, such as streptavidin, have been found to be stable in solution at up to 80° C. (Bang's Labs).

Avidin when directly coated on the chip is able to bind any biotinylated reagent with the requisite sensitivity which is comparable to a monolayer and superior to less stable multilayers. When formed at higher avidin concentrations than described herein or with silane layers as described in US20110053139 (incorporated by reference), the process is liable to not bind avidin with the same affinity as the present process and tends to wash off during biosensor use. However, the direct coating process of the present invention provides sufficient biotin binding sites to permit attachment of specific reagents with a coating stability that persists even after binding of large biotinylated antibodies that react with one or both of the still available biotin binding sites. These characteristics are maintained even when exposed to hydrodynamic stresses from fluidic forces during washes or upon warming.

Figure 4:
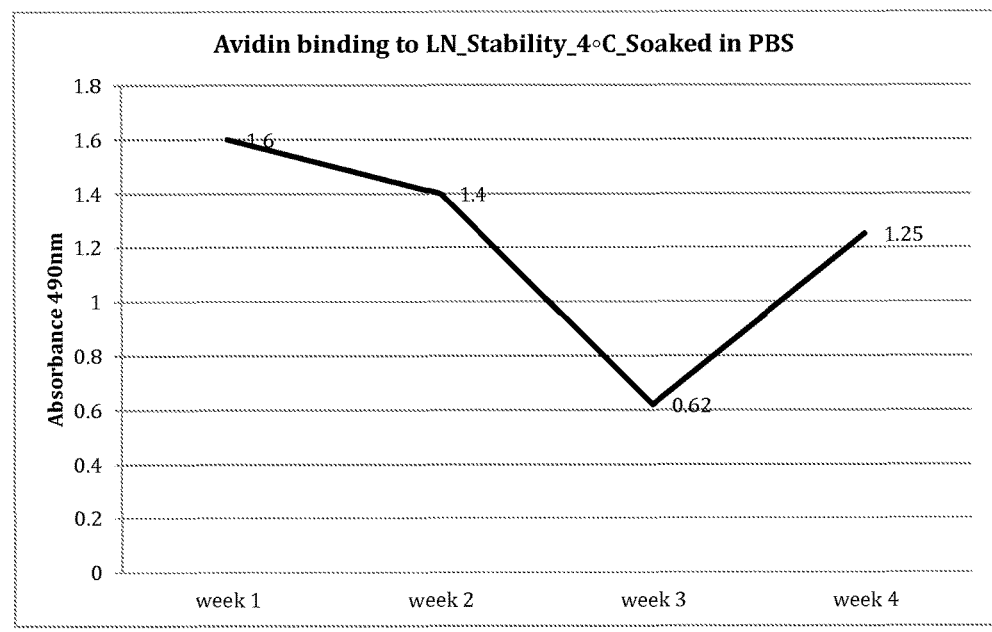

As shown in FIG. 4 different types of avidins can be used in coating and are also very stable. FIG. 4 shows the optical density of avidin bound to lithium niobate over a period of one month stored at 4° C. The chip was prepared according to the methods of the present invention. After a vigorous wash with PBS, the chips were stored submerged in sterile PBS and placed in 4° C. for up to one month. Once per week, a positive control (+avidin) and a negative control (−avidin) chip were tested with biotin horse radish peroxidase assay using o-phenyl diamine dihydrochloride tablets (Sigma)]. After a substrate and stop reaction solution (sulfuric acid 2.5 m) were added, the O.D. in FIG. 4 was read with a Bio-Tek Synergy HT plate reader. The O.D. shows that the binding of avidin to the chip is just as prevalent as when initially bound.

The excellent thermal stability of the generic avidin biosensor (aka biosensor component), in the immobilized state, is of importance in any POC tests that will be used in tropical climates without easy access to refrigerator storage. The generic avidin biosensor thus does not need protective coatings but it needs to be kept sealed, preferably in a nitrogen atmosphere. Stabilization of target specific antibody formulations in a stabilizing glassy state inside single-use ready to use specimen treatment tubes is accomplished by the PAFRA™ process (U.S. Pat. No. 5,098,893 and EP 0223221) which has been successfully used for room temperature storage of labile enzymes. A coating buffer containing preservatives such as sugar and glycerol can be used for example.

C. Indirect Coating Method In addition to coating the crystal surface directly, the process described herein can be used to coat avidins on other materials including pre-coatings of the prior art (without limitation) to coat the crystal surfaces. Wider applications are also possible: for example, directly making avidin-coated magnetic or latex particles or lateral flow membranes which are currently made in multiple steps. Sodium silicate or silicon dioxide is often used to coat surfaces to protect shear horizontal waves as a wave guide. The avidin binding process of the present invention binds well to silicone dioxide or glassy surfaces so that it can be superimposed on a wave guide surface. In addition, the process has application in the capture of avidin in an irreversible glassy layer that is converted to a silica-Nay layer with acid, giving both binding and a silica guiding layer as taught in US 2011/0053139. In other embodiments, metal ions coated on the crystal surface, such as Silver (which binds and blackens the surface), copper, gold or iron can provide the substrate for indirect coating for the processes disclosed herein. Both silver or gold salts also bind and form a surface binding thiol and disulfide proteins like IgG, and avidins.

Avidin was coated on a silica (SiO2) coating deposited on the surface of a piezoelectric material by contacting a lithium niobate crystal with a sodium silicate solution Avidin was then bound to the silica coating as described above for the direct binding.

Figure 5:
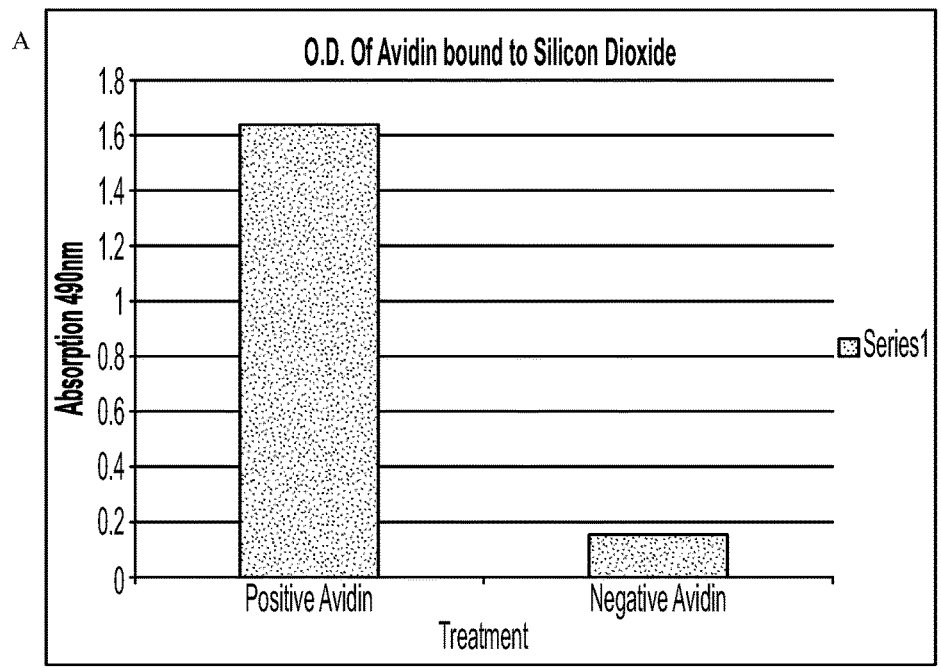
Figure 5:
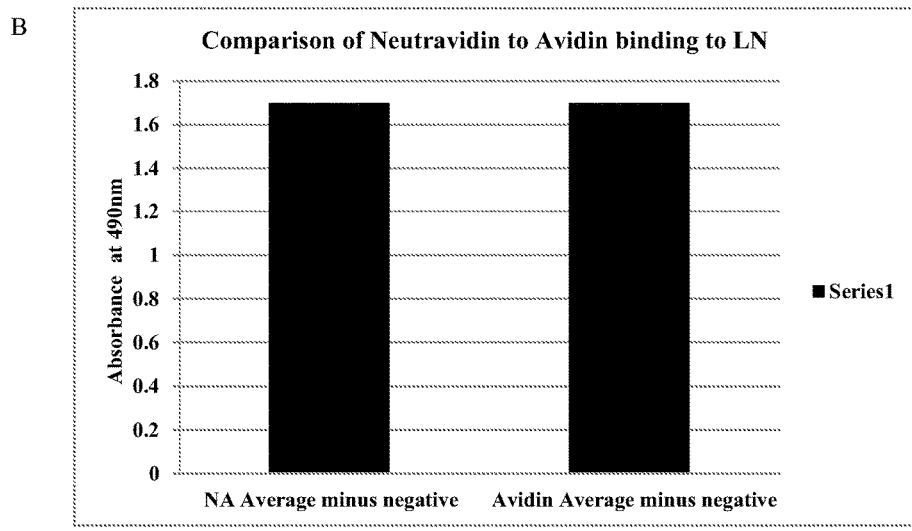

As shown in FIG. 5, avidin does bind to SiO2 to coat Lithium Niobate using methods described herein. After an extensive PBS wash and a blocking step, Biotin HRP was added to the chip and incubated for 45 minutes at RT. A substrate was added to induce color change of HRP enzyme for 20 minutes, followed by the addition of a stop solution. In FIG. 5, Panel A, the absorption (O.D.) was read at 490 nm. The O.D. for avidin bound to the silicon dioxide is shown in on the left column and the silicon dioxide without avidin is shown on the right. Subtracting the negative (0.2) from the positive (1.6), the O.D. reading is still 1.4, which is considered to be good binding for avidin. (FIG. 5, Panel B compares the binding of avidin with neutravidin. Both avidin and neutravidin have approximately the same O.D. However, the avidin and neutravidin in this experiment were coated directly on the piezoelectric surface. Panel B presents averages from two positive avidin measurements after subtraction of a negative measurement.)

D. Binding of Analytes to the Coated Biosensor

In some embodiments, the bound avidin on the crystal surface requires activation to bind analytes of interest. The activation includes a biotinylated binder such as an antibody, which is specific to an analyte antigen of interest. The antibody or other agent is biotinylated prior to its affixation to the avidin-coated chip. The antibody can bind to its analyte antigen either after it is affixed to the avidin substrate or before. The analyte biotinylated antibody complex can be formed outside of the sensor and then the complex can be contacted with the sensor, whereby the biotin on the antibody will bind to the avidin-coated chip. Which of the two methods is preferred is dependent upon the analyte and on the sample processing. Both methods are within the scope of the present invention. Analysis of the surface coating with a particular antibody bound to avidin on the chip surface resulted in a determination for depth of 6 to 9 nm, again using AFM, demonstrating that antibody is indeed bound to the avidin layer. (See FIG. 2)

Antigen-specific biotinylated capture reagents are applied to form a second layer consisting of bound and excess free biotinylated reagent in a non-drying medium also containing protein stabilizers known in the art such as, but not limited to, sucrose, trehalose, glycerol and the like. Many agents can be biotinylated, the most commonly used amongst them is biotinylated antibodies, specifically recognizing an analyte of interest. Protein capture reagents can be biotinylated chemically or enzymatically. Chemical biotinylation utilizes various known conjugation chemistries to yield nonspecific biotinylation of amines, carboxylates, sulfhydryls and carbohydrates. It is also understood that N-hydroxy succinimide (NHS)-coupling gives biotinylation of any primary amines in the protein. Enzymatic biotinylation results in biotinylation of a specific lysine within a certain sequence by a bacterial biotin ligase. Most chemical biotinylation reagents consist of a reactive group attached via a linker to the valeric acid side chain of biotin. Enzymatic biotinylation is most often carried out by linking the protein of interest at its N-terminus, C-terminus or at an internal loop to a 15 amino acid peptide, termed AviTag or Acceptor Peptide (AP). These biotinylation techniques are known.

The capture reagent can be an antibody or aptamer or other specific ligand or receptor formed from any of the following; biotinylated oligonucleotides, nucleotides, nucleic acids, (Pon, Richard T. (1991). "A long chain biotin phosphoramidite reagent for the automated synthesis of 5'-biotinylated oligonucleotides". *Tetrahedron Letters* 32 (14): 1715-8), proteins, peptides, and antibodies including IgA, IgG, IgM, IgE, enzymes, enzyme co-factors, enzyme inhibitors, membrane receptors, kinases, Protein A, Poly U, Poly A, Poly Lysine receptors, polysaccharides, chelating agents, carbohydrate, sugars.

Once bound the capture reagent is briefly exposed to heated air to effect partial removal of water from the applied fluid forming a protective and stabilizing gel that will ensure long-term stability of bound proteinaceous binders like antibodies in a non-drying gel layer which allows essentially complete time-dependent formation of the second antigen-specific binder layer. These glass-like layers are optionally dehydrated for storage in the presence of desiccant pellets of silica or molecular sieves inside the pouch of the cartridge. The upper chamber of the cartridge is sealed to form a fluidic compartment The cartridge with chamber is then sealed inside a plastic storage pouch, preferably in a $N_2$ atmosphere.

Figure 6:
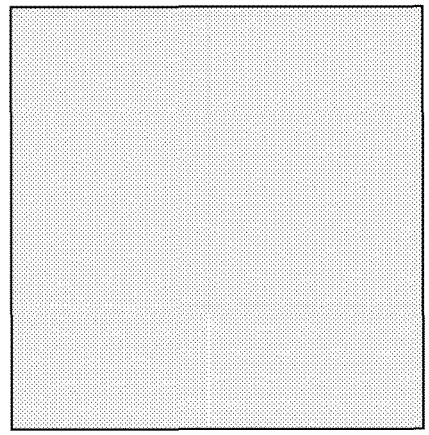
Figure 6:
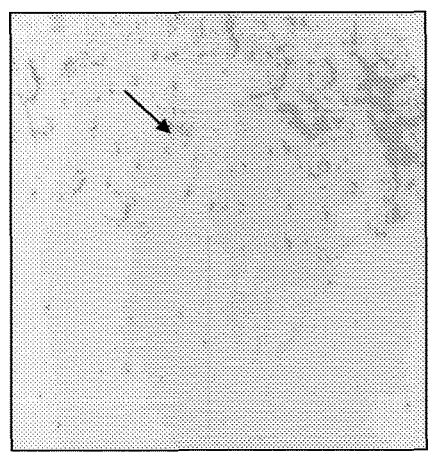
Figure 6:
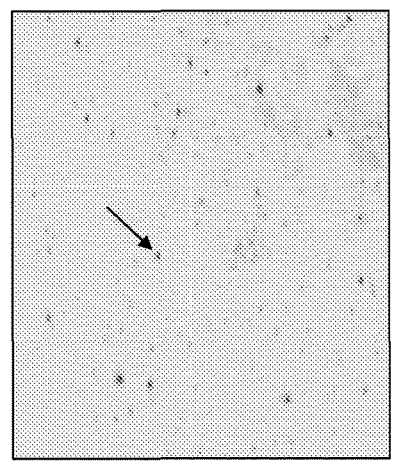
Figure 7:
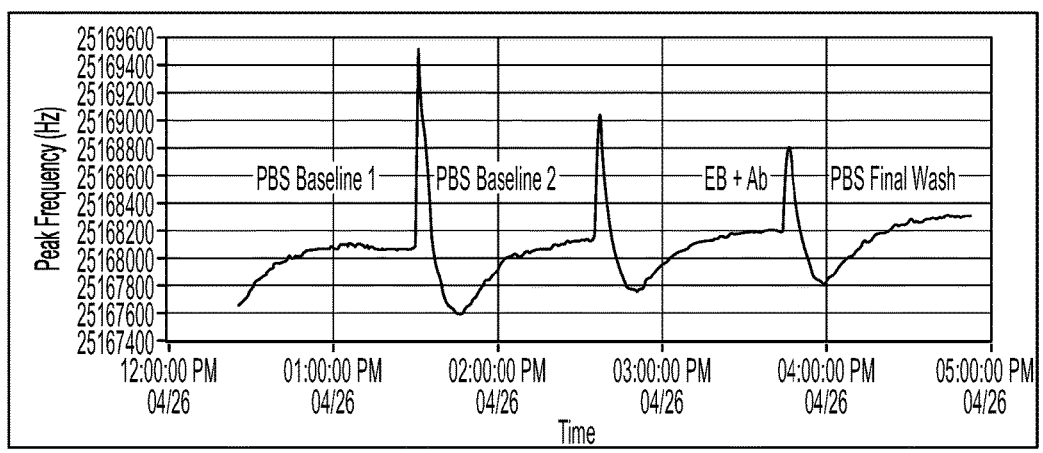

The binding between anchor substance (avidin) and biotinylated capture reagent causes a second, capture reagent layer to form on the chip. Prior to use, any residual unbound biotinylated capture reagent and other components in the protective gel layer can be readily removed by a simple flush with an assay buffer or even with the specimen fluid during the analytical procedure. These sensors have been demonstrated to detect antigens, as shown in FIGS. 6 and 7. When the capture reagent is an antibody, it can be applied in amounts ranging (for example and without limitation) from 0.025 to 25 µg/ml.

E. Binding of Analytes and Disease Detection Using the Biosensor

Biosensors according to the invention can be easily produced in mass quantities to detect a variety of agents and biochemical markers when outfitted with the appropriate right biofilm coating which contains a capture agent that specifically binds to the analyte of interest. Examples of the uses to which this integrated biosensor can be put include human and veterinary diagnostics. Analyte is defined as any substance that is or that is found in or generated by an infectious agent and that can be used in detection including without limitation an oligonucleotide, nucleic acid, protein, peptide, pathogen fragment, lysed pathogen, and antibody including IgA, IgG, IgM, IgE, enzyme, enzyme co-factor, enzyme inhibitor, toxin, membrane receptor, kinase, Protein A, Poly U, Poly A, Poly Lysine, polysaccharides, and chelating agents. Detection of antigen-antibody interactions has been previously described (U.S. Pat. Nos. 4,236,893, 4,242,096, and 4,314,821, all of which are expressly incorporated herein by reference). Further, the application in the detection of whole cells (including procaryotic (such as pathogenic bacteria) and eukaryotic cells, including mammalian tumor cells); viruses (including retroviruses, herpes viruses, adenoviruses, lentiviruses, etc.); fungus, parasites and spores, included phenotypic variations, of infections agents, such as serovars or serotypes are within the scope of the invention.

F. Types of Piezoelectric Materials

Many piezoelectric materials are suitable for use in the present invention without limitation. Also included without limitation are polished wafers of all sizes which are commercially available in diverse crystal orientation that are particularly suitable for propagation of surface acoustic waves in either the surface acoustic (SAW) or bulk acoustic wave (BAW) modes. Although it is preferred that the crystal be polished on both sides, single polished materials are also suitable some applications. All varying crystal orientations are encompassed within the scope of the present invention. Also suitable are langasite crystals. Examples are lead magnesium niobate/lead titanate (PMN-PT), lead zirconate niobate/lead titanate (PZN-PT), lithium niobate (LiNbO$_3$), lithium niobate with dopants, lithium tetraborate (Li2B4O$_7$), lithium tantalate and quartz without limitation. Barium titanate (BaTiO$_3$) is also a non-lead source of piezoelectric crystals for room temperature applications.

Examples of other crystals that could be used in the present invention include the following: berlinite (leaky saw), gallium orthophosphate (rayleigh), potassium niobate (SAW and BAW candidate), barium zirconititanate, lanthan calcium oxoborate (possible for future saw), langasite crystals (like lanthanum gallium silicate); ceramics such as ceramic perovskite structures (KNbO3, Ba2NaNb5O5, SrTiO3, Pb2KNb5O15, bismuth ferrite, NaxWO), lead zirconate titanate (for resonators or transducers), cadmium sulphide (normally light resistor sensors), zinc oxide (could be applied as a film due to reactivity of OH groups), gallium arsenide, bismuth and germanium oxide (optics/insulator), aluminum nitride (as piezo film), and polyvinylidene fluoride (PVDF film).

In addition, multi-crystal elements could be used. In particular, they would be appropriate to propagate waves in multiple directions for various purposes. Also, piezoelectric films can be bonded to non-piezoelectric materials in a sandwich format and thus such constructs are not a priori excluded from the invention.

2. Acoustic Wave Sensors

For a piezoelectric crystal resonator, acoustic waves travel within the bulk of the crystal (i.e. bulk modes) or on the surface of the crystal, both are found in several forms. Bulk acoustic waves ("BAW") travel through the crystal medium and the commonly used BAW devices are thickness shear mode (TSM), acoustic plate mode (APM), and shear horizontal plate mode (SH-APM). Commonly used SAW devices include Shear Horizontal Surface Acoustic Wave (SH-SAW), surface traverse wave (STW) and Love Wave (LW). In a biosensor, these waves should not be attenuated or they lose their ability to detect analytes in biological fluids with the requisite sensitivity. Regardless of wave type, preserving the coupling of the mass change without significantly attenuating the wave is a significant problem in developing a sensor. In the present invention while all these wave modes are considered, the ultimate mode choice will need to be highly sensitive to biological mass change without attenuating the wave when in contact with fluid. The configuration of the sensor is also important in achieving this goal. Thus, the structure of the sensors of the invention and the nature of the waves used with each are subject to optimization.

Because bulk waves travel through the crystal material, they were thought to be less sensitive as biosensors. Bulk wave sensitivity needs to be preserved with a simple, consistent biocoating, such as provided by the present invention, since sensitivity is lost when the mass binding is further removed from the generated bulk wave and the correlation between mass and wave frequency is lost or weakened. Thus, bulk waves can be used with the anchor substance coating according to the present invention.

In addition, the biocoating has to be easy to apply and consistent from device to device or the variability between devices will make them difficult to use in a health care setting where treatment is based on diagnosis and diagnostic accuracy depends on device sensitivity (while specificity depends primarily on the capture reagent). In addition, the chosen biocoating has to bind the capture reagent consistently and reproducibly, or the variability will result in missed or inaccurate diagnosis (as was the case with prior art devices comprising silane, hydrogel or polymer coatings which did not consistently provide uniform coating layers and which did not bind proteins with consistent strength).

While surface generated waves are more sensitive to mass changes, conventional SAW devices such as STW are often a poor choice for biological fluids, since they penetrate into the biological fluid to a considerable depth, thereby damping the wave. The SH-SAW provide better biosensors since the waves are horizontally polarized, however they need to be protected by a wave guide.

The present invention overcomes many of the problems surrounding the use of various types of surface acoustic waves as biosensors. This is done through the use of a new piezoelectric biosensor configuration which in some embodiments utilizes the described Acoustic Plate Mode (APM) waves, but in other embodiments can employ alternative wave forms such as SH-SHEAR, as described herein.

The result is a rapid, cost-effective system for the analysis of biological samples in aqueous fluids. In some embodiments, this is accomplished, in part, by providing a fluid-impervious barrier between a surface (or portion) of the piezoelectric medium in contact with fluids and the opposite surface or an isolated portion of the piezoelectric crystal with which the two (2) IDT elements are in contact. The barrier can be in the form of a leak proof chamber in which the fluids are confined. The portion of the piezoelectric medium that, upon use of the device will be in contact with a fluid sample, forms one wall of the chamber. The result is a simple integrated biosensor suitable for detection of target entities in aqueous biological fluids.

This new biosensor also comprises a biofilm chip which can bear a novel direct coating in accordance with the invention or can bear an indirect coating with the superimposition of an intermediate layer as described above. A specific embodiment of the present invention is thus an integrated chip wherein the biofilm and a dedicated APM mode piezoelectric biosensor form the analytical component of a platform for a POC diagnostic device and where the analytical component is described in accordance with the present invention.

In some embodiments, the present invention incorporates new chemistries in the biocoating process and improves upon the piezoelectric sensor to yield a new piezoelectric biosensor configuration utilizing Acoustic Plate Mode Waves generated from IDTs which is located on the surface and flanking the capture reagents which are used in the molecular detection of target entities. APM's are separated or shielded from interfering lateral waves traveling as a Rayleigh Wave along the plane of the IDTs. In other specific embodiments, the present invention incorporates a biosensor design having a shielded electrical component like IDT's and electrical connections in an insulating film located on either side of a fluid chamber containing a sensing surface. The sensing surface contains a non-insulated area which is specifically coated with one or more layers of immobilized reagents, including a target-specific capture reagent designed to capture target entities in a fluid sample. The volume of the biological fluid sample is determined by the dimensions of the fluid compartment attached to the sensing surface. The wave perturbations of the APM signal generated from bound target entities are detected by sensitive commercial signal analyzers, e.g. network analyzers, such as those manufactured by Agilent.

The present invention improves upon the prior art used in commercial or experimental biosensors by incorporating APM in a piezoelectric biosensor whereby the APM is able to respond with high sensitivity to a frequency change on the opposing side of a piezoelectric surface without the need for layer guiding or a wave guide. The present invention further considers the use of capture layers as discussed in US Published App. No 2011/0136262, incorporated by reference, and others which utilized microchannels for multiplexed analysis of target events in rapid detection of infectious agents, fragments thereof, and derived toxins or proteins in biological samples.

Some biosensor embodiments of the invention can resemble in certain respects conventional SH-SAW based sensors Thus, for example, in some embodiments, the present biosensor also uses a piezoelectric surface which can be for example niobate, quartz, silica or tantalate based (among a choice of other materials provided herein), sets of input and output IDTs located on the same piezoelectric surface as a target specific binder layer typically formed by overlaying numerous sequentially deposited lower layers, capture of target molecules from fluid specimens, and detection of bound targets as changes in the nature of the wave due to the bound mass. The biosensors of the invention based on these prior art sensors employ a very simple method of applying an anchor coating as described below.

However, other embodiments differ in additional significant respects from SAW biosensors reported in the prior art by utilizing bare or non-insulated regions along the piezo surface where bound targets are located while the acoustic wave is generated on the opposite side and traverses the substance of the crystal. Instead of using Rayleigh waves to detect the molecules on the surface, APM (bulk or Plate-Mode waves) are used to sense the attached molecules in liquid phase on the opposite side. Unlike Rayleigh waves, APM is able to operate in liquid and detect the changes on the opposite surface. According to the experimental results, APM has a high Q factor (>1000) in IF range. A higher Q factor yields higher sensitivity and more frequency changes.

Some embodiments of the present invention thus employ the APM mode. FIG. 10 shows a theoretical model for Rayleigh waves and APM on a 128° YX-Cut or a Z cut LiNbO3 substrate for application in the present invention. The sensing area corresponds to the fluid chamber where the biological sample to be tested is placed at the top of the piezoelectric substrate. The wave is generated at the bottom and moves through the piezoelectric medium to detect the analyte bound to the top surface (via an avidin molecule affixed directly to the surface), upon encountering the extra mass of the captured analyte, the frequency of the wave will change. So while either 128° YX-Cut or a Z cut has been described in FIG. 10, other cuts are considered in the present invention which can be optimized to provide the same or about the same sensitivity by routine experimentation. A further embodiment incorporates a ZX cut for APM as described by Andle, J. C. et al, Sensors and Actuators B 24-25 (1995) 129-133: "Selective acoustic plate mode DNA sensor."

In another embodiment, SAW waves are used to detect molecular binding on the opposite side of 128° YX-Cut LiNbO3 substrate. The bound molecular masses interfere with the SAW and change their reflections. The changes in frequency can be measured in multiple ways such as the measurement of shifts in the center frequency of the harmonic.

Two embodiments for the biosensor are schematically depicted in FIG. 11A and FIG. 11B. FIG. 11A shows a biosensor cartridge or housing (10) having contact points (1). Piezoelectric substrates capable of producing APM waves such as LiNbO$_3$ are some of the suitable choices with the preferred material being, 128° YX-Cut or Z cut lithium niobate (LiNbO$_3$) in some embodiments. The biochip further includes an Inter Digital Transducer (IDT) as an IDT wave generator (2) an IDT wave receiver (3) and other electrical components in an insulated region of the functionalized surface of the functionalized bare crystal. The insulator can be composed for example of known polymeric insulating films. The biological fluid sample containing the target entities or analytes enters a fluid chamber (4) through the inlet port (5) after a preliminary filtration through optional filter (6). The capture reagent (7) is affixed to the non-insulated area of the functionalized surface. Binding of the antigen (8) to the receptor (7) creates a perturbation in the flow of the APM wave from the IDT wave generator (2) across the fluid chamber which is detected as a modified APM wave (modification reflected in its frequency) by the IDT wave receiver (3) on the opposite side. The fluid filter (6) on the fluid inlet port is optionally needed to exclude potential non-specific binding (NSB) due to larger non-target particulates. The fluid then exits the chamber through outlet port (9). The fact that the IDTs are on an opposite surface can be illustrated in FIG. 10 which although theoretical, shows the configuration.

FIG. 11B illustrates a coated biosensor according to the invention having multiple channels: an analyte channel 15, a positive control channel 16 and a reference channel 17. Elements (1-6) in FIGS. 11A-11B correspond to (1-6) in FIG. 10. (7) is an outlet port, (8) is an output connector, (9) is an input connector 10 is the crystal substrate.

3. Multi-Array Devices

A further embodiment of the present invention is the manufacturing of a single, disposable cartridge system that encompasses a single sensor or multiple sensors utilizing a variety of wave modes and enhancements. Each cartridge incorporates, at a minimum, a sensor and a system for encapsulating the sensor and handling fluids within a fluid cartridge. Utilization of the sensor may be either through a direct wired contact with the reader system or through a wireless mode.

In the simplest embodiment, each sensor incorporates electronic elements applied to piezoelectric substrates and/or biological elements. FIG. 11A illustrates one embodiment of the sensor with a single delay line structure for use in the Acoustic Plate Mode (APM mode). In the APM mode, the electronic elements are applied on the opposite side of the substrate relative to the side where the biological and fluidic elements come into contact. In other wave modes (such as SAW or SH-SAW), these elements may be placed on the same side of the substrate as the biological and fluidic elements, either with or without the addition of a wave guide. Piezoelectric substrates capable of producing APM waves are encompassed within the scope of this embodiment. One example is a material that is, 128° YX-Cut or Z cut lithium niobate (LiNbO$_3$). Other embodiments incorporate SH-SHEAR WAVES. The wave guide is typically composed of polymers but may also be made through combinations of polymers or metals either in combination or alone. The delay line incorporates contact points (1) and Inter Digital Transducers (2) and (3). The contact points (1) may not be required if a wireless system is used to interrogate the circuit. The Inter Digital Transducers (IDTs) are embodied in matched pairs (or multiple matched pairs) with each set including an IDT wave generator (2) and IDT wave receiver (3). In some embodiments, the generator and receiver may be the same. Other elements considered to be incorporated include, but are not limited to, the use of reflectors, amplifiers, additional grounds, absorbers or insulators composed of known polymeric insulating films.

The non-electronic elements of the sensor are shown in FIG. 11A. The fluid cartridge contains a fluidic chamber (4), inlet port (5), and optional in-line filter (6). The biological fluid sample containing the target entities or analytes enters the fluid chamber (4) through the inlet port (5) after a filtration through optional in-line filter (6). The fluidic chamber (4) may be on the same side as the electronics (as is the case in an SH-SAW mode) or opposite side (for use as an APM mode sensor). The fluidic chamber (4) is the pre-defined area where the biological fluid sample comes into contact with the substrate (either with or without biofilm or other modification). The capture reagent (7) is affixed to an area of the piezoelectric substrate surface (as defined by the area of the fluidic chamber (4) which may or may not be insulated. Binding of the antigen (8) to the receptor (7) creates a perturbation in the flow of the APM wave from the IDT wave generator (2) across the fluid chamber which is detected as a modified APM wave (modification reflected in its frequency, amplitude, phase or other derived information) by the IDT wave receiver (3) on the opposite side. The fluid filter (6) on the fluid inlet port is optional but may be needed to exclude potential non-specific binding agents (NSB) due to larger non-target particulates. The fluid then exits the chamber through outlet port (9) to a waste container.

FIG. 11B illustrates an embodiment of an APM mode sensor with three delay lines in a parallel configuration: an active delay line, a positive control delay line and a reference delay line. This structure could be expanded to include additional delay lines or multiple sensors to configure a multi-array single, disposable system, to diagnose a single infectious element or condition, quantify the level of infection or disease or distinguish between closely associated diseases, diseases with similar symptomology or frequently concurrent infections, such as sexually transmitted disease panels. Sensors with multiple delay lines or multiple sensors could also be positioned in a side by side, staggered or radial configuration.

EXAMPLE 1

Manual Processes for Coating of Biosensor Chips Bearing Neutravidin and Biotinylated Antibody All of these methods have been actually performed.

a. Coating without fixation: Clean and activate LiNbO$_3$ surfaces for about 1-10 sec at atmospheric pressure with a plasma generating device (e.g. Plasma Treat USA, Elgin, Ill.) before application of avidin which is accomplished by inkjetting avidin in a solution containing 50% glycerol in PBS at an avidin concentration of 0.5 mg/ml, followed with brief drying using warm air from a heat gun at about 50° C. or drying at room temperature for about 30 min to bond the avidin to the surface, the biosensor is now ready for use or packaging.

Optionally, deposition of neutravidin is followed by a fixing step.

b. Coating with thermal fixation: Neutravidin is applied by ink jetting as described in Example 1a. The neutravidin may be fixed to the piezo substrate by heating to about 30-50° C. with an infrared heat lamp for up to 30 min.

c. Coating with solvent fixation: The coated area of the biosensor made in Example 1a and heat gun dried; it is then exposed for about 15 seconds to a stream of air saturated with 100% isopropanol or acetone, made by bubbling through these solvents, followed by brief exposure to a stream of N$_2$ gas.

d. Coating with vapor: Immobilized neutravidin as in Ex. 1a is fixed by heat drying followed by exposure to an air stream saturated with formaldehyde which is made by bubbling air through a solution of 10% formaldehyde and aimed at the dried neutravidin layer for about 15 sec, followed with N$_2$ gas for about 15 seconds.

e. Attaching biotinylated antibody to avidin coating on chip: The selected antibody to a particular analyte is biotinylated using a commercially available kit (e.g., Innova Bioscience or Fisher Scientific). The biotinylated antibody is diluted using 0.05% BSA/PBS buffer to the desired concentration. This antibody preparation is incubated on the avidin fixed chip at room temperature for 15-60 minutes, based on the known affinity of the antibody provided in the manufacturer's specifications.

EXAMPLE 2

Automated Coating Processes a. Automated Direct Coating Mode for Neutravidin Biosensors:

Online manufacturing of some embodiments involves deposition of neutravidin coating on piezo crystals affixed to the lower portion of the biosensor housing that is then mounted on a conveyor belt. After plasma treatment, the sensor is moved to the neutravidin inkjetting station and coated with 5-10 µl of fluid containing 0.01 to 5.0 mg/ml neutravidin; or 0.01-2.0 mg/ml; or 0.01-1.0 mg/ml by weight per 0.5 cm square area. The fluid is evaporated and the neutravidin fixed on the biosensor by brief exposure to heat from a heat gun (about 50° C.). The upper cover of the housing is then affixed to form the leak proof fluid chamber of the biosensor cartridge.

b. Automated Coating Mode for Coated Neutravidin Having Biotinylated Antibody:

A similar inkjet process as described above in 2a is used to coat the biotinylated antibody diluted to a suitable dilution in a non-drying stabilizing gel matrix of 0.01 M PBS-0.1% BSA, pH 7.4, 1-10% trehalose, 1-5% glycerol, 0.05% sodium azide at room temperature, followed by partial evaporation with warm air from a heat gun for about 1 min. The gel coating on the biosensor is left on the surface to complete reaction of the biotinylated antibody with the immobilized neutravidin during subsequent storage in a plastic pouch.

c. Automatic Coating Mode for Coated Avidin Bearing Biotinylated Oligonucleotide:

The process of Example 2b is performed, but a biotinylated oligonucleotide is diluted in a gel matrix instead.

d. Assembly and Packaging: After the coating process in steps a, b, or c, the upper portion of the cartridge housing is attached to form the fluidic chamber that is fully separated from the electronic components on the reverse side of the chip.

The automated coating processes of this example can also be practiced on conventional-type sensors (i.e., those with intermediary coatings), as well as on sensors in which the intermediary oxide coatings have been applied with simple two-step processes according to embodiments of the present invention.

EXAMPLE 3

*Chlamydia trachomatis* Detected on the Biosensor

Experiments were conducted with *C. trachomatis*, an obligate intracellular bacterium which causes a sexually transmitted disease in both women and men. The procedures used to coat avidin and antibody are described in Example 1. The antibody used is a monoclonal antibody against the major outer membrane (MOMP) of *C. trachomatis* (Abcam) biotinylated and used at 0.25 µg/ml. *C. trachomatis* was obtained from Microbia and was suspended in PBS/Buffer at a concentration of $10^5$ per ml in a similar experiment, monoclonal antibody directed against *C. trachomatis* elementary body lipopolysaccharide (Medix). A aliquot of elementary bodies (EB) of $10^5$ EB+0.25 µg/ml of biotinylated anti-EB LPS was incubated for 30 minutes at RT and then added to the chip. FIGS. 6 and 7 depict the results of experiments conducted with these specific infectious antigens. FIG. 6 is a series of black and white tracings of a fluorescent microscopy slide taken of an AMT chip bearing *C. trachomatis* elementary bodies bound to antibody bound to neutravidin. Section A depicts the image of a negative control (chip has only avidin and no antibody), the revealing agent is nucleic acid DAPI for section B and FITC-labeled anti-antitrachomatis antibody for Section C. This experiment confirmed the presence of cellular material on the chip, which shows that antigen was bound to the immobilized antibody in turn bound to an avidin anchor.

FIG. 7 is a plot of frequency over time and shows the frequency shift with the binding of *chlamydia* to anti-*chlamydia*. The chip was prepared with avidin as described in Example 1 and assembled in the cartridge as described above. Two 1-hour (1×) PBS baseline measurements were performed to ensure stability of the chip. The gradual incline of frequency is due to a temperature change in the fluid. It would eventually settle after 30 minutes (not shown). The antibody-antigen mixture was incubated for 30 minutes at room temperature and then added to the chip in the third segment for 1 hour. The fourth segment is the reading after the chip was vigorously washed with PBS. A frequency shift was obtained from subtracting the final wash from baseline 1, yielding a value of 223.66 Hz and showing EB bound to the chip.

The sensors used the configuration schematically described in FIG. 11, but had a single channel and were assembled using multiple layers of acrylic and several layers of adhesive and transparency sheets to create a form-fitted cartridge around the sensor, with exposures in the bottom for the contact point of the sensors and on the top, inlet and outlet ports. The experiments were done using an Agilent HP 8753E signal analyzer. A frequency shift of 800 MHz was observed in this experiment between baseline buffer administered after which the antibody was administered and then finally the *Chlamydia* antigens. The frequency shift remained despite a final wash, indicating that the antigen was responsible for the change in frequency of the acoustic plate mode sensor.

EXAMPLE 4

Dengue Virus Detected on the Biosensor

Figure 8:
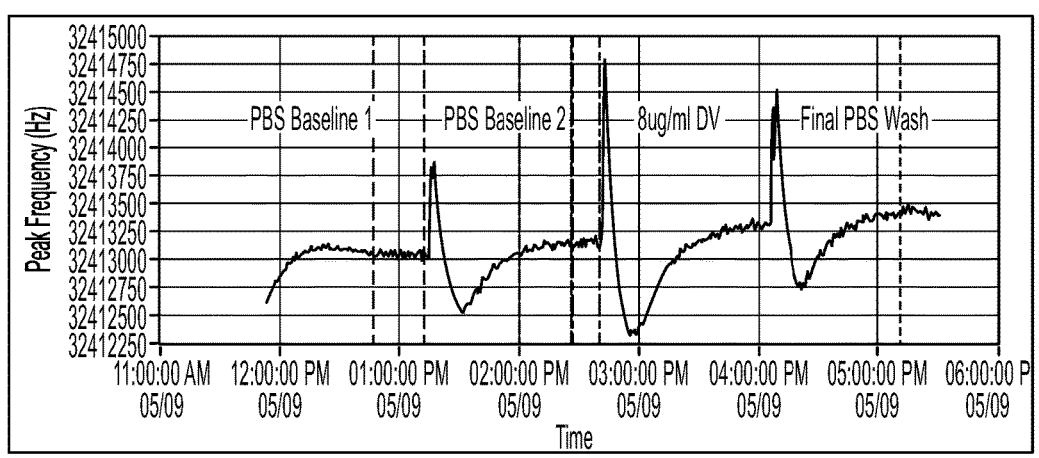

The procedures used to coat avidin and antibody are described in Example 1. FIG. 8 depicts the frequency shift for experiments conducted with dengue virus when suspended in PBS buffer. Dengue virus is a flavivirus which causes dengue fever, affecting about 100 million people every year. It is transmitted by an urban dwelling mosquito, Aedipus egyptii. Four serotypes are known, though only one serotype causes the infection at any one point in time. Serotypes can change over several years. Serotype 2 is the most common serotype currently known. The experiments for dengue virus employed a monoclonal envelope protein to Serotype 2 antibody (Feldan) at 4 µg/ml in 0.05% BSA-PBS, incubated for 30 minutes at room temperature. PBS wash was performed to remove excess antibody. The dengue type 2 antigens were obtained from Microbix. The virus was suspended in standard (1×) PBS/Buffer ($10^4$ per ml or 8/2 g/ml) concentration of the commercially available stock (this resembles the extent of human viremia under acute infection conditions). The acoustic plate mode sensors and wave generator were the same as in Example 3. A frequency shift of 500 MHZ was observed between baseline buffer (control) and the sensor after application and attachment of the antibody preparation followed by application of the dengue virus antigens. The frequency shift remained despite a final wash, indicating that the antigen was responsible for the change in frequency of the acoustic plate mode sensor. The results are shown in FIG. 8 which is a plot of peak frequency against time and demonstrates the frequency shift. Two PBS (1×) baseline measurements were performed to ensure stability of chip, 1 hour each. Dengue virus was added to the chip in the third segment for 1 hour. The fourth segment is the reading after the chip was vigorously washed with extra PBS. A frequency shift was determined by subtracting the final wash from baseline 1 to obtain a value of 278.62 Hz, showing that the virus bound to the chip.

EXAMPLE 5

Protein Detection

Figure 9:
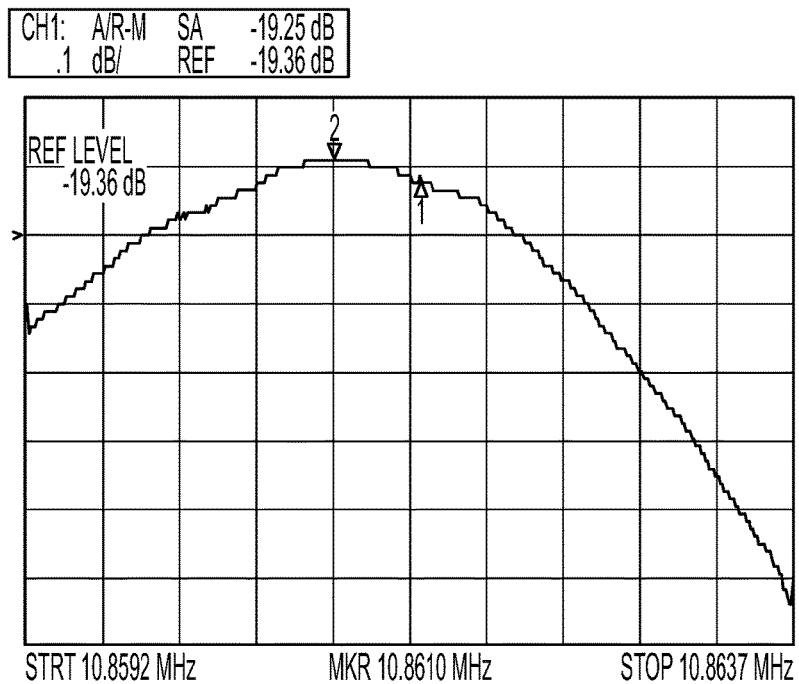

FIG. 9 is a graph of frequency v. time and depicts the frequency shift seen before and after the chip was exposed to antibody. The process used to coat this antibody is described in Example 1. The sensor was the same as in Example 3. Arrow 1 shows the frequency received from the sensor when only avidin has been bound to it. Arrow 2 shows the frequency received from the sensor after antibody was applied. The antibody was a polyclonal antibody against elementary bodies of *C. trachomatis* biotinylated and used at 1:200 dilution. (Abeam, Cambridge, Mass.—AV20387). A change in 100 MHZ is seen, the shift occurring due to the addition of antibody to the chip.

Unless defined otherwise, all technical and scientific terms used herein have the same meanings as commonly understood by one of ordinary skill in the art.

\* \* \*

Those skilled in the art will recognize, or be able to ascertain using no more than routine experimentation, many equivalents to the specific embodiments of the invention described herein. Such equivalents are intended to be encompassed by the following claims.

All patent and other documents cited herein are incorporated by reference in their entirety.

The invention claimed is:

1. An acoustic wave biosensor component comprising a piezoelectric crystal comprising a layer of an anchor substance directly and irreversibly bound chemisorptively as a monolayer and without an intermediary coating to a crystal surface of the piezoelectric crystal, the anchor substance having the property of binding to a capture reagent comprising a specific binding partner for the anchor substance.

2. The biosensor component of claim 1 wherein the anchor substance is an avidin, neutravidin, or streptavidin.

3. The biosensor component of claim 1 wherein the piezoelectric material is selected from the group consisting of langanite crystals, lead magnesium niobate, lead titanate, lead zirconate niobate, lead titanate, lithium niobate, lithium niobate with dopants, lithium tetraborate, lithium tantalite, quartz, barium titanate, berlinite, gallium orthophosphate, potassium niobate, barium zirconititanate, lanthan calcium oxoboratem, langasite crystals, lanthanum gallium silicate, ceramic perovskite structures, bismuth ferrite, lead zirconate titanate, cadmium sulphide, zinc oxide, gallium arsenide, bismuth and germanium oxide, aluminum nitride, and polyvinylidene fluoride.

4. The biosensor component of claim 1 wherein the anchor substance is an oligonucleotide or a polynucleotide.

5. The biosensor component of claim 1 further comprising an acoustic wave generator and an acoustic wave receiver.

6. The biosensor component of claim 5 wherein the wave generator generates a wave selected from the group consisting of thickness shear mode, acoustic plate mode, horizontal plate mode, shear horizontal surface acoustic wave, surface traverse wave, and love wave.

7. A process for coating the surface of a piezoelectric material with biofilm comprising an anchor substance having the property of binding to a capture reagent comprising a specific binding partner for the anchor substance, the process comprising:
   a. treating by plasma treatment a crystal surface of a piezoelectric material to increase the surface energy of the crystal surface;
   b. applying a layer of the anchor substance directly and irreversibly without an intermediary coating to the crystal surface; and
   c. forming a chemisorbed anchor layer as a monolayer on the crystal surface.

8. The process of claim 7 wherein the plasma treatment comprises exposure to an atmospheric plasma jet stream for approximately 5 to 10 seconds.

9. The process of claim 7 wherein the piezoelectric material is selected from the group consisting of langanite crystals, lead magnesium niobate, lead titanate, lead zirconate niobate, lead titanate, lithium niobate, lithium niobate with dopants, lithium tetraborate, lithium tantalite, quartz, barium titanate, berlinite, gallium orthophosphate, potassium niobate, barium zirconititanate, lanthan calcium oxoboratem langasite crystals, lanthanum gallium silicate, ceramic perovskite structures, bismuth ferrite, lead zirconate titanate, cadium sulphide, zinc oxide, gallium arsenide, bismuth and germanium oxide, aluminum nitride, and polyvinylidene fluoride.

10. The process of claim 7 wherein the applying step comprises spraying or contact transferring the anchor substance onto the surface layer to form a thin uniform liquid film as a microdot on the surface.

11. The process of claim 10 wherein the applying step further comprises drying the anchor layer.

12. The process of claim 7 wherein the anchor substance is an avidin, neutravidin, or streptavidin.

13. The process of claim 7 further comprising contacting the layer of bound anchor substance with a composition comprising a capture reagent, wherein the capture agent has the property of specifically recognizing an analyte in a biological fluid and causing the capture reagent to bind to the anchor substance through a specific binding partner of the anchor substance.

14. An acoustic wave biosensor comprising:
   a. a piezoelectric crystal comprising a layer of an anchor substance directly and irreversibly bound chemisorptively as a monolayer and without an intermediary coating to a crystal surface of the piezoelectric crystal, the anchor substance in the layer being also bound to a capture reagent, wherein the capture reagent comprises a specific binding partner for the anchor substance and specifically recognizing an analyte present in a biological fluid;
   b. an acoustic wave generator, the generator generating a wave wherein a reaction between the capture reagent and an analyte causes a detectable change in properties of the acoustic wave; and said biosensor further comprising a chamber for receiving a biologic fluid sample.

15. The biosensor of claim 14 wherein the capture reagent specifically recognizes an analyte selected from the group consisting of whole cells, bacteria, eukaryotic cells, tumor cells, viruses, fungus, parasites, and spores, and fragments, proteins, nucleic acid and toxins of any of the foregoing.

16. The biosensor of claim 14 wherein the capture reagent is specific for *Chlamydia trachomatis* or Dengue virus.

17. The biosensor of claim 14 further comprising a plurality of channels on the biocoated piezoelectric crystal, wherein each channel comprises a different capture reagent layer, or is a control channel comprising no capture reagent, the channels permitting a plurality of analyses to be conducted simultaneously.

18. A method for determining the presence or quantity of an analyte in a biological fluid sample the method comprising:
- contacting the component of claim 1 with a composition comprising a capture reagent the capture reagent comprising or constituting a specific binding partner for the anchor substance and also specifically recognizing an analyte;
- causing the capture reagent to bind to the anchor substance, forming a capture reagent layer;
- contacting the bound capture reagent layer with a biological fluid sample;
- generating an acoustic wave across the piezoelectric surface; and
- measuring any change in amplitude, phase or frequency of the acoustic wave resulting from the analyte binding to the capture reagent layer.

* * * * *